United States Patent [19]

Semeraro et al.

[11] Patent Number: 4,946,851
[45] Date of Patent: Aug. 7, 1990

[54] 1,4-DIHYDROPYRIDINES

[75] Inventors: Claudio Semeraro, Bresso; Dino Micheli, Carpi; Daniele Pieraccioli; Giovanni Gaviraghi, both of Verona, all of Italy; Alan D. Borthwick, London, England

[73] Assignee: Glaxo, Sp.A., Italy

[21] Appl. No.: 266,233

[22] Filed: Oct. 28, 1988

Related U.S. Application Data

[63] Continuation of Ser. No. 16,256, Feb. 19, 1987, abandoned.

[30] Foreign Application Priority Data

Feb. 20, 1986 [IT] Italy ........................... 19481 A/86

[51] Int. Cl.$^5$ .................. A61K 31/455; C07D 211/86
[52] U.S. Cl. .................................. 514/332; 514/356; 546/321; 546/263
[58] Field of Search ................ 546/321, 263; 514/332, 514/356

[56] References Cited

U.S. PATENT DOCUMENTS 4,492,703  1/1985  Goldmann et al. ................ 546/321

FOREIGN PATENT DOCUMENTS 1409865  10/1975  United Kingdom .
2105989A  4/1983  United Kingdom .

Primary Examiner—Jane T. Fan
Attorney, Agent, or Firm—Morgan & Finnegan

[57] ABSTRACT

Compounds are described of the formula

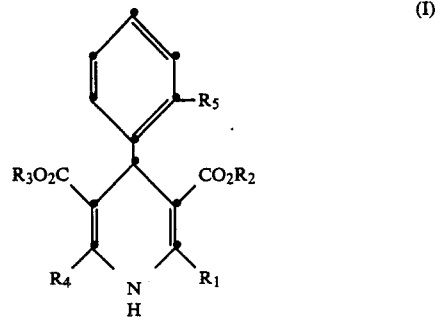

(I)

wherein
$R_1$ and $R_4$ independently represent a $C_{1-4}$ alkyl group;
$R_2$ and $R_3$ independently represent a $C_{1-6}$ straight or branched alkyl chain or alkoxy group;
$R_4$ represents a $C_{1-4}$ alkyl group;
$R_5$ represents a group $CH=CR_6R_7$ where $R_6$ is a hydrogen atom or $C_{1-3}$ alkyl group and $R_7$ represents an aryl, pyridyl or cyano group; or $R_5$ represents the group $C\equiv CR_8$ where $R_8$ is an aryl group.

The compounds represented by formula (I) reduce intracellular calcium ion concentration by limiting transmembranal calcium ion influx and thus may be useful for the treatment of cardiovascular disorders such as hypertension.

18 Claims, No Drawings

1.4-DIHYDROPYRIDINES

This application is a continuation of Ser. No. 016,256, filed Feb. 19, 1987 now abandoned.

This invention relates to novel heterocyclic derivatives which have an effect on the transmembranal influx of calcium ions into the cells of cardiac and smooth muscle, to processes for the preparation thereof, to pharmaceutical compositions containing them and to their use in therapeutics.

The role of intracellular calcium ions in the control of the contractile system of cardiac and smooth muscle is well known. It has been established that compounds which limit the intracellular calcium ion concentration by preventing or reducing the transmembranal calcium ion influx in cells of the contractile system of cardiac and smooth muscle are useful in the treatment of cardiovascular disorders.

We have now found a new group of compounds which reduce intracellular calcium ion concentration by limiting transmembranal calcium ion influx and thus may be useful for the treatment of cardiovascular disorders such as hypertension, angina pectoris, myocardial ischaemia, congestive heart failure, cerebral vascular and peripheral disorders, and for the treatment of diseases characterised by reversible airway obstruction such as asthma and chronic bronchitis.

The invention thus provides for compounds of the general formula (I).

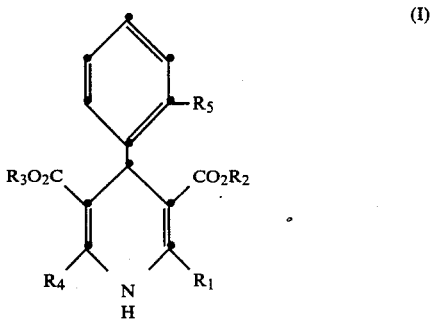

(I)

wherein $R_1$ and $R_4$ independently represent a $C_{1-4}$ alkyl group;

$R_2$ and $R_3$ independently represent a $C_{1-6}$ straight or branched chain alkyl or alkoxyalkyl group;

$R_5$ represents a group $CH=CR_6R_7$ where $R_6$ is a hydrogen atom or $C_{1-3}$ alkyl group and $R_7$ represents an aryl, pyridyl or cyano group; or $R_5$ represents the group $C|CR_8$ where $R_8$ is an aryl group.

The compounds represented by formula (I) can exist in more than one isomeric and/or enantiomeric form and the invention includes all such isomers, enantiomers and mixtures thereof.

For the groups $R_7$ and $R_8$ the term aryl means a phenyl group optionally substituted by one or more halogen atoms e.g. fluorine, chlorine, bromine or iodine or $C_{1-4}$ alkyl or $C_{1-4}$ alkoxy groups.

Examples of suitable groups for $R_1$ and $R_4$ include methyl or ethyl groups.

Examples of suitable groups for $R_2$ and $R_3$ independently include $C_{1-4}$ straight or branched alkyl such as methyl, ethyl, isopropyl, isobutyl, t-butyl or $C_{1-4}$ alkyl (such as methyl, ethyl or n-propyl) substituted by a $C_{1-3}$ alkoxy e.g. methoxy or propoxy group.

A preferred group of compounds of formula (I) are those wherein $R_1$ and $R_4$ represent methyl.

A further preferred group of compounds of formula (I) are those in which $R_2$ and $R_3$ independently represent a methyl or ethyl group, more especially ethyl.

When $R_5$ represents the group $C|CR_8$ examples of suitable groups for $R_8$ include phenyl optionally substituted by one or two chlorine or bromine atoms or by a methyl group or a methoxy or ethoxy group. More preferably $R_8$ represents an unsubstituted phenyl group.

Where $R_5$ represents the group $CH=CR_6R_7$ examples of suitable groups for $R_6$ include a hydrogen or a methyl, ethyl or propyl group or more particularly a hydrogen atom. Examples of the group $R_7$ include cyano, pyridyl or a phenyl group optionally substituted by one or two chlorine or bromine atoms, a methyl group or a methoxy group. More preferably $R_7$ represents a phenyl group optionally substituted by a chlorine atom or a methyl or methoxy group.

A preferred class of compounds of the invention are those of formula (I) wherein $R_1$ and $R_4$ represent methyl, $R_2$ and $R_3$ represent ethyl, $R_6$ represents hydrogen and $R_7$ represents a phenyl group optionally substituted by a chlorine atom or by a methyl or methoxy group or $R_8$ represents a phenyl group.

The ability of compounds of the invention to limit or inhibit the effect of calcium ions on the tone of vascular smooth muscle may be determined using a depolarised rabbit ear artery prepared according to the method of Towart. R. et al Br. J. Pharmacol. 1982, 75, 1508.

The antihypertensive activity of compounds of the invention may be demonstrated by intravenous and/or oral administration of the compound to male spontaneously hypertensive rats.

The compounds of the invention are thus of interest in the treatment of hypertension. They are also potentially useful for the treatment of other cardiovascular disorders including angina pectoris, myocardial ischaemia, congestive heart failure, cerebral vascular and peripheral disorders and diseases characterised by reversible airways obstruction such as asthma and chronic bronchitis.

The compounds of the invention may be formulated in a conventional manner for use with one or more pharmaceutical carriers or excipients.

Thus a further aspect of the invention includes pharmaceutical compositions the compounds of formula (I) and/or physiologically acceptable addition salts thereof formulated for oral, sub lingual, transdermal, parenteral or rectal administration, or for administration by inhalation or insufflation.

A proposed daily dosage of active compound of the invention for the treatment of man is in the range of 0.03 mg to 100 mg, which may conveniently be administered in one or more doses. The precise dose employed will depend on the age and condition of the patient as well as the route of administration.

For oral use the compounds of the invention are conveniently administered to the human patient at a dose in the range 0.3 to 100 mg per day. For parenteral use the compounds of the invention are conveniently administered at a dose in the range of 0.03–30 mg per day.

For administration by inhalation use the compounds of the invention are conveniently administered to the human patient at a dose in the range of 0.1 mg to 10 mg per day.

For oral use the compound is preferably administered twice or more particularly once a day.

Methods for preparing the compounds of formula (I) are described below and for the intermediates described below $R_1$-$R_8$ have the meanings defined above for compounds of formula (I) or are such groupings in a protected form unless otherwise stated.

Thus compounds of formula (I) in which $R_5$ represents the group CH=$CR_6R_7$, may be prepared by reaction the α,β-unsaturated ketone (II) with the aminoester (III). The reaction is conveniently carried out in a solvent such as an alkanol, e.g. ethanol or isopropanol and preferably with heating e.g. 40°–150° C.

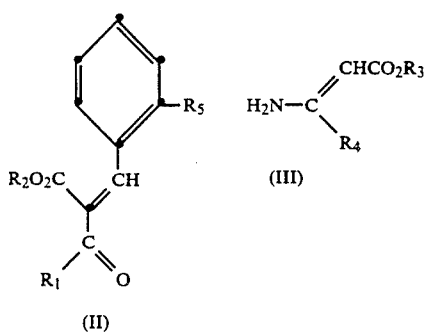

The α,β-unsaturated ketone (II) may be prepared by reacting the aldehyde (IV) with the ketoester (V), in a solvent such as an alkanol e.g. ethanol or isopropanol, preferably with heating e.g. 40°–150° C. Conveniently this reaction is carried out in the presence of a catalyst such as piperidine acetate.

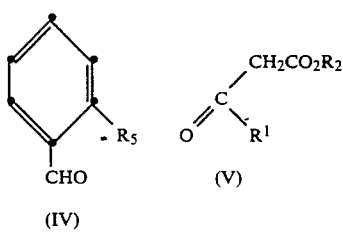

In a modification of this process for preparing compounds of formula (I), the aldehyde (IV) may be reacted with a mixture of the aminoester (III) and the ketoester (V) under the conditions previously described for the reaction of the α,β-unsaturated ketone (II) with the aminoester (III).

Compounds of formula (I) in which $R_1$ and $R_4$ are the same and $R_2$ and $R_3$ are the same may be prepared by reacting the aldehyde (IV) with the aminoester (III) in the presence of a suitable acid catalyst. Examples of suitable acid catalysts include organic acids such as oxalic acid, alkanoic acids e.g. acetic acid or haloalkanoic acids such as trichloroacetic acid or trifluoroacetic acid or pyridinium salts thereof, or a sulphonic acid such as an alkanesulphonic acid e.g. methanesulphonic acid or an arylsulphonic acid e.g. benzenesulphonic acid or p-toluenesulphonic acid or a tetrahaloboric acid such as tetrafluoroboric acid. The reaction is preferably carried out in the presence of a solvent and at a temperature within the range of −70° to 30° C. preferably −30° to 10° C. Suitable solvents, for the reaction include aprotic solvents such as hydrocarbons, e.g. hexane or cyclohexane, acetonitrile or ethers such as tertiary butyl methyl ether, dioxan or tetrahydrofuran, or protic solvents such as an alkanol e.g. methanol, ethanol, propanol, isopropanol or butanol.

In yet another process of the invention the compounds of formula (I) in which $R_5$ represents the group CH=$CR_6R_7$ may be prepared by reacting compound (VI):

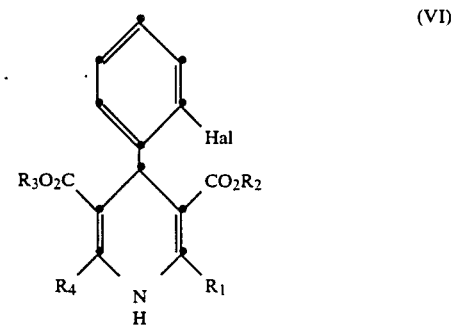

(where Hal represents a bromine or iodine atom), with the ethylene derivative $CH_2$=$CR_6R_7$ (VII) in which $R_6$ and $R_7$ are as defined in formula (I). The reaction is carried out in the presence of a catalytic amount of a palladium salt such as palladium acetate, and a suitable organic base such as a trialkylamine e.g. triethylamine or tri-n-butylamine. The reaction is also preferably carried out in the presence of a triarylphosphine such as tri-o-tolyphosphine, or more preferably, triphenylphosphine.

The reaction is conveniently carried out in a suitable solvent such as xylene or t-butyl acetate, or more conveniently in dimethylformamide or in a mixture of solvents e.g. xylene/dimethylformamide, preferably with heating. The reaction mixture is preferably heated within the temperature range of 80° C. to 150° C., more preferably at 100° C. to 110° C.

Compounds of formula (IV), in which $R_5$ represents the group CH=$CR_6R_7$ may be prepared by reacting the bis aldehyde (VIII) with the triphenylphosphorane (IX) in solvent such as methylene chloride or toluene.

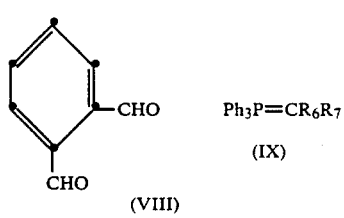

Compounds of formula (IV) may also be prepared by reacting a 2-halobenzaldehyde (X)

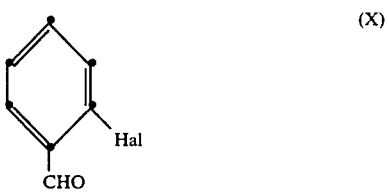

(where Hal represents a bromine or iodine atom) with the ethylene derivative (VII). The reactions take place under the conditions previously described for the reaction between the compound of formula (VI) and the ethylene derivative (VII).

The compounds of formula (VI) may be prepared by reacting the 2-halobenzaldehyde (XI) with the aminoester (III) and/or the ketoester (V) according to the conditions described above for the reaction between the compound of formula (IV) and the aminoester (III) and/or the ketoester (V).

Compounds of formula (I) in which $R_5$ represents the group $CH=CR_6R_7$ may also be prepared from the reaction of the compound (XI) with the phosphorane (IX) in a suitable solvent such as dichloromethane, tetrahydrofuran or toluene. Preferably the reaction is carried out with heating for example 40°–120° C., conveniently at reflux.

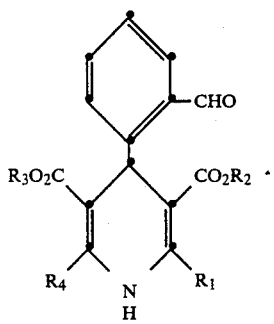

(XI)

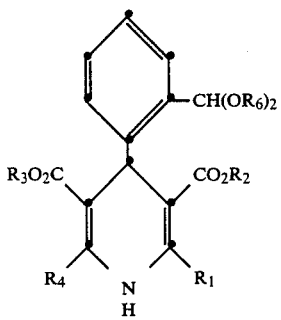

(XII)

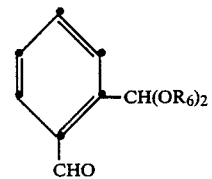

(XIII)

The intermediate (XI) may be prepared by aqueous acid hydrolysis of the corresponding acetal (XII; in which $R_6$ represents an alkyl group).

The compound of formula (XII) may be prepared from the aldehyde (XIII) by reaction with a compound of formula (III) and/or (V) under the conditions described above for preparing compounds of formula (I) from the intermediate (IV). The intermediate (XIII) may be prepared from the bromobenzene derivative (XIV) by reaction with butyl lithium in solvent followed by addition of dimethylformamide.

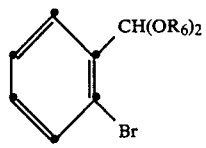

(XIV)

The compounds of formulae (III), (V), (VII) and (IX) are either known compounds or may be prepared by analogous methods to those described for known compounds.

Compounds of formula (I) in which $R_5$ represents the group $-C|CR_8$ may be prepared from the protected acetylene derivative (XV):

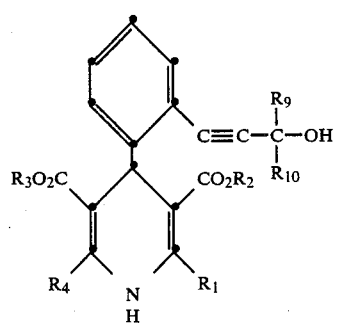

(XV)

wherein $R_1, R_2, R_3$ and $R_4$ are as described above in formula (I) and $R_9$ and $R_{10}$ independently represent a $C_{1-4}$ alkyl group e.g. methyl group.

The compounds of formula (I) wherein $R_5$ represents the group $C|CR_8$ and $R_8$ is an optionally substituted phenyl group, may be prepared from the reaction of the protected acetylene derivative (XV) with the appropriate halobenzene derivative ($R_8$Hal) where Hal represents a chlorine, bromine or iodine group. The reaction is conveniently carried out in the presence of a strong base such as potassium hydroxide or sodium hydroxide, a triarylphosphine palladium salt such as bis(triphenylphosphine) palladium (II) dichloride, and a copper (I) halide e.g. cuprous iodide. Conveniently the reaction is carried out in a solvent, for example piperidine and preferably with heating.

Compounds of formula (XV) may be prepared from the aldehyde (XVI) by reaction with the ketoester (V) and/or the aminoester (III) under conditions similar to those described above for the reaction of the aldehyde (IV) with compound (V) and/or (III).

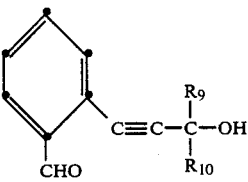

(XVI)

Compounds of formula (XVI) may be prepared from the reaction of the halobenzaldehyde (X) with the propargyl alcohol $CH|CC(R_9R_{10})OH$ (XVII) in the presence of a cuprous salt e.g. cuprous iodide, and a triarylphosphine palladium salt, e.g. bis(triphenylphosphine)palladium (II) dichloride. The reaction is carried out in a solvent such as piperidine and preferably with heating. The propargyl alcohols (XVII) are either known compounds of may be made by analogous methods to those described for the known compounds.

The following examples illustrate the invention. Temperatures are in °C.

Intermediate 1

3-(2-Formylphenyl)-2-propene nitrile

A solution of triphenylphosphoranylidene acetonitrile (13 g) in dry dichloromethane (20 ml) was added to a solution of ortho phthalaldehyde (5.4 g) in dry dichloromethane (20 ml), at 0°. The solution was stirred at room temperature for 1 h, then the solvent evaporated and the oil taken up with diethyl ether. The solid was filtered, washed with ether and the solution evaporated to dryness to give a yellow oil, which was eluted on a silica gel column (gradient petrol ether/diethyl ether, 1:1) to give the (E)-isomer of the title compound (0.9 g) and the (Z)-isomer of the title compound (2 g) (eluted first) as white solids which were recrystallized from petrol ether/diethyl ether (9:1).

(E) isomer: m.p. 87°–89°; T.l.c. (petrol ether/diethyl ether, 6:4). Rf 0.40.

(Z) isomer: m.p. 82°–83°; T.l.c (petrol ether/diethyl ether, 6:4). Rf 0.45.

Intermediate 2

[1-(2-Formyl)phenyl-3-hydroxy-3-methyl]-1-butyne

A mixture of 2-bromobenzaldehyde (9.5 g), 2-methyl-3-butyn-2-ol (5 g), copper (I) iodide (0.05 g), bis[triphenylphosphine]palladium (II) dichloride (0.7 g) in piperidine (200 ml) was stirred for 6 h at 60°. The solution was filtered, evaporated and was then treated with ethyl acetate. The organic phase was washed with dilute acid and brine, dried over $Na_2SO_4$ and the solvent was evaporated. The residue was purified by column chromatography on silica gel eluting with ethyl acetate/cyclohexane 1:1 to give the title compound (8 g) as a green oil.

Microanalysis for $C_{12}H_{12}O_2$ requires: C76.57;H6.43. found: C74.51;H6.47%.

Intermediate 3

2,6-Dimethyl-4-(2-[(3-hydroxy-3-methyl)-1-butynyl]-phenyl)-1,4-dihydro-3,5-pyridinedicarboxylic acid, diethyl ester Ethyl-3-aminocrotonate (28.85 g) in anhydrous ethanol (100 ml) was added dropwise to a solution of Intermediate 2 (8.5 g) and trifluoroacetic acid (12.75 g) in anhydrous ethanol (80 ml) at −5° to −10°. The mixture was stirred for 4 h at −10°. To the reaction was added a solution of sodium bicarbonate (200 ml) and then the mixture was extracted with tert-butylmethylether. The organic phase was washed with water, dried over $Na_2SO_4$ and evaporated. The residue was purified by column chromatography on silica gel eluting with ethyl acetate/cyclohexane 1:1 to give the title compound (9.5 g) as a yellow solid. M.p.=141.3°.

Intermediate 4

4-(2-Bromophenyl)-1,4-dihydro-2,6-dimethyl-3,5-pyridine-carboxylic acid, diethyl ester (a) A solution of 2-bromobenzaldehyde (83.7 g) in absolute ethanol (1350 ml) was cooled to −10° under stirring. To the solution trifluoroacetic acid (108 g) was added quickly followed by a solution of ethyl 3-aminocrotonate (146 g) in ethanol (750 ml) added dropwise during 1 hour. Stirring was continued for a further 1 hour at −10° and the mixture was then added dropwise to a 0.3% solution of hydrochloric acid (7000 ml) under vigorous stirring. The solid was collected by filtration, washed with water and petroleum ether and dried in vacuo at 60° to give the title compound (156 g). m.p. 142°–143°. T.l.c. (ethyl acetate/petroleum ether, 8:2) Rf=0.5.

(b) A solution of 2-bromobenzaldehyde (10.8 g), ethyl 3-aminocrotonate (9.36 g) and ethyl acetoacetate (9.12 g) in absolute ethanol (50 ml) was heated at reflux for 15 hours. The mixture was then cooled, diluted with absolute ethanol (250 ml) and added dropwise to a 0.2% solution of hydrochloric acid (2000 ml) under vigorous stirring. The solid was collected by filtration, washed with petroleum ether (150 ml) and dried in vacuo to give the title compound (19.3 g) m.p. 142°–143°.

EXAMPLE 1

(E)-4-(2-(2-Phenylethenyl)phenyl)-1,4-dihydro-2,6-dimethyl-3,5-pyridinedicarboxylic acid diethyl ester A solution of (E)-1-formyl-2-(2-phenylethenyl)benzene (1.65 g) in ethanol (20 ml) was cooled to 0° and then trifluoroacetic acid (1.22 ml) added followed by a solution of ethyl-3-aminocrotonate (5.116 g) in ethanol (20 ml). The mixture was stirred at 0° for 5 h then a further quantity of trifluoroacetic acid (1.22 ml) was added and after a further h at 0°, the mixture was stirred at 10° for 1½ h. The mixture was evaporated and the residue taken up in dichloromethane (60 ml), washed with 10% hydrochloric acid, dried ($MgSO_4$) and evaporated. The residue was purified by column chromagraphy on silica eluting with ethyl acetate/petroleum, 3:7 to give the crude product which crystallized from ethyl acetate/petroleum ether to give the title compound (1.67 g) M.p. 187°–188°.

Analysis found: C,75.1;H,6.8;N,3.2. $C_{27}H_{29}NO_4$ requires: C,75.2;H,6.8;N,3.3%.

EXAMPLE 2

(E)-4-(2-(2-Phenyl-2-methylethenyl)phenyl)-1,4-dihydro-2,6-dimethyl-3,5-pyridinedicarboxylic acid, diethyl ester To a solution of Intermediate 4 (1.633 g) α-methyl styrene (0.65 ml) and tri-n-butylamine (1.19 ml) was added palladium acetate (0.009 g), tri-o-tolylphosphine (0.073 g) and xylene (3 ml). The mixture was stirred under an atmosphere of nitrogen at 100° for 24 h. A further quantity of palladium acetate (0.009 g) and tri-o-tolylphosphine (0.049 g) was added and the mixture stirred at 100° for a further 24 h. The mixture was cooled to room temperature diluted with ethyl acetate (50 ml), filtered, and the filtrate washed with 10% hydrochloric acid, water and brine, dried ($MgSO_4$) and evaporated. The residue was purified by column chromatography on silica eluting with petroleum 40°–70°/ethyl acetate, 7:3 to give an oil which was triturated with petroleum ether (40°–70°) and the solid crystallized from petroleum ether (40°–70°) to give the title compound (0.32 g). M.p. 141°–142°.

Analysis found: C,75.6;H,7.0;N,3.2. $C_{28}H_{31}NO_4$ requires: C,75.5;H,7.0;N,3.1%.

Examples 3–6 were similarly prepared from Intermediate 4 and the appropriate alkenylene derivative.

EXAMPLE 3

4-(E)(2-(2-(4-Methoxyphenyl)ethenyl)phenyl)-1,4-dihydro-2,6-dimethyl-3,5-pyridinedicarboxylic acid diethyl ester M.p. 179°–181°. T.l.c. (petrol/ethyl acetate 6:4) Rf 0.4. from 4-methoxy styrene.

EXAMPLE 4

(E)-4-(2-(2-(4-Methylphenyl)ethenyl)phenyl)-1,4-dihydro-2,6-dimethyl-3,5-pyridinedicarboxylic acid, diethyl ester M.p. 192°–195°.

Analysis found: C74.73;H6.93;N3.09. $C_{28}H_{31}NO_4$ requires: C75.47;H6.95;N3.14%, from 4-methyl styrene.

EXAMPLE 5

(E)-4-(2-(2-Cyano-1-propenyl)phenyl)-1,4-dihydro-2,6-dimethyl-3,5-pyridinedicarboxylic acid, diethyl ester M.p. 119°–121°.

Analysis found: C70.02;H6.70;N7.04. $C_{23}H_{25}N_2O_4$ Requires: C70.04;H6.64;N7.09%. from 2-cyano-1-propene.

EXAMPLE 6

E-4-(2-(2-(4-Chlorophenyl)ethenyl)phenyl)-1,4-dihydro-2,6-dimethyl-3,5-pyridinedicarboxylic acid, diethyl ester M.p. 178°–181° C. T.l.c. (petrol/ethyl acetate 6:4) Rf 0.40 from 4 chlorostyrene.

EXAMPLE 7

(E)-4-(2-(2-Cyanoethenyl)phenyl)-1,4-dihydro-2,6-dimethyl-3,5-pyridinedicarboxylic acid, diethyl ester Ethyl 3-aminocrotonate (4.7 g) was added to a solution of the (E) isomer of intermediate I (2.7 g) in acetic acid (50 ml), at room temperature for 2 h, then poured into water and extracted with ethyl acetate. The organic phase was washed with 5% $NaHCO_3$, then with water and dried over $Na_2SO_4$. Evaporation of the solvent gave a dark oil which was eluted on a silica gel column (gradient petrol ether/diethyl ether, 1:1) to give a yellow solid which was recrystallized from diisopropyl ether to yield the title compound. M.p. 172°–173°. T.l.c. (methylene chloride/ethyl acetate, 8:2). Rf 0.54.

EXAMPLE 8

(Z)-4-(2-(2-Cyanoethenyl)phenyl)-1,4-dihydro-2,6-dimethyl-3,5-pyridinedicarboxylic acid, diethyl ester Ethyl 3-aminocrotonate (5.3 g) was added to a solution of the (Z) isomer of Intermediate 1 (1.6 g) in acetic acid (100 ml), at room temperature. The solution was stirred at room temperature for 3 h, then poured into water. The red solid obtained from water was triturated into water, then dissolved in ethyl acetate, washed with 5% $NaHCO_3$, then with water and dried over $Na_2SO_4$.

Evaporation of the solvent gave a pale yellow solid which was recrystallized from diethyl ether to yield the title compound. M.p. 130°–132°. T.l.c. (methylene chloride/ethyl acetate, 8:2) Rf 0.52.

EXAMPLE 9

2,6-Dimethyl-4-(E)-(2-[(2-phenyl)-1-ethynyl]phenyl)-1,4-dihydro-3,5-pyridinedicarboxylic acid, diethyl ester A mixture of Intermediate 3 (1 g), sodium hydroxide pellets (0.3 g), bromobenzene (0.44 g), bis[triphenylphosphine]-palladium (II) dichloride (0.04 g) and copper (I) iodide (0.003 g) in piperidine (30 ml) was refluxed for 7 hours. The solution was filtered, evaporated and the residue taken up with ether (100 ml). The organic phase was washed with dilute acid and brine, dried over $Na_2SO_4$ and evaporated. The residue was crystallised from methanol to give the title compound (0.25 g) as a white solid. M.p. 181°.

Microanalysis for $C_{27}H_{27}NO_4$ requires C75.50;H6.34;N3.26, found C75.28;H6.34;N3.26%.

EXAMPLE 10

(E)-4-(2-Ethynyl)phenyl)-1,4-dihydro-2,6-dimethyl-3,5-pyridinedicarboxylic acid, diethyl ester Intermediate 3 (5 g) in toluene (20 ml) was treated with sodium hydroxide pellets (0.75 g) and refluxed for 4 h. The solid was filtered off and the solvent evaporated to obtain a brown solid. Crystallisation from methanol/water gave the title compound (3 g) as a white solid. M.p. 181°–182°.

Microanalysis for $C_{21}H_{23}NO_4$ requires: C71.37;H6.56;N3.98, found: C71.54;H6.57;N4.00%.

EXAMPLE 11

4(E)-[2-(2-Pyridineethenyl)phenyl]-1,4-dihydro-2,6-dimethyl-3,5-pyridinedicarboxylic acid diethylester A mixture of Intermediate 4 (1.5 g) 2-vinylpyridine (0.39 ml), palladium acetate (3.2 g), tri-o-tolylphosphine (44 mg) and triethylamine (1.5 ml) was heated in a capped bottle at 100° for 48 h. The cooled solid reaction mixture was poured in ethyl acetate and the solid was filtered off. The resulting clear solution was evaporated to dryness to give a brown oil which was purified by flash chromatography eluting with ethyl acetate/petroleum ether 1:1 to give the title compound (250 mg) as white solid. M.p. 192°–195°. T.l.c. (ethyl acetate/petroleum ether 1:1) Rf 0.3.

We claim:

1. A compound of general formula (I)

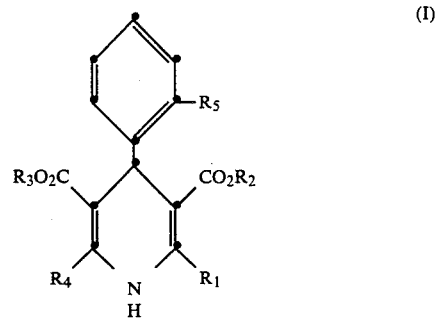

wherein, $R_1$ and $R_4$ independently represent a $C_{1-4}$ alkyl group;

$R_2$ and $R_3$ independently represent a $C_{1-6}$ straight or branched chain alkyl or a $C_{1-4}$ alkyl group substituted by a $C_{1-3}$ alkoxy group;

$R_5$ represents a group $CH=CR_6R_7$ where $R_6$ is a hydrogen atom or $C_{1-3}$ alkyl group and $R_7$ represents a phenyl group optionally substituted by one or more halogen atoms or $C_{1-4}$ alkyl or $C_{1-4}$ alkoxy groups, pyridyl or cyano group; or $R_5$ represents the group $C|CR_8$ where $R_8$ is a phenyl group optionally substituted by one or more halogen atoms or $C_{1-4}$ alkyl or $C_{1-4}$ alkoxy groups.

2. A compound as claimed in claim 1 wherein $R_1$ and $R_4$ represent a methyl group.

3. A compound as claimed in claim 1 wherein $R_3$ and $R_2$ independently represent a methyl or ethyl group.

4. A compound as claimed in claim 1 wherein $R_6$ represents hydrogen.

5. A compound as claimed in claim 1 wherein $R_7$ represents a cyano, pyridyl or a phenyl group, optionally substituted by one or two chlorine or bromine atoms, a methyl or methoxy group or $R_8$ represents a phenyl group optionally substituted by one or two chlorine or bromine atoms or a methyl or methoxy group.

6. A compound as claimed in claim 1 wherein $R_7$ represents a phenyl group optionally substituted by a chlorine atom or a methoxy or methyl group or $R_8$ represents a phenyl group.

7. A compound as claimed in claim 1 in which $R_3$ and $R_2$ independently represent a methyl or ethyl group, $R_6$ represents hydrogen, $R_5$ represents the group $C|CR_8$ where $R_8$ is a phenyl group optionally substituted by one or more halogen atoms or a $C_{1-4}$ alkyl or a $C_{1-4}$ alkoxy group and $R_7$ represents a cyano, pyridyl or a phenyl group optionally substituted by one or two chlorine or bromine atoms, a methyl or methoxy group.

8. A compound as claimed in claim 7 in which $R_2$ and $R_3$ each represent an ethyl group.

9. A compound as claimed in claim 7 in which $R_3$ and $R_2$ each represent a methyl group.

10. A compound as claimed in claim 7 in which $R_5$ represents the group $C|CR_8$ where $R_8$ is an unsubstituted phenyl group.

11. A compound as claimed in claim 1 in which $R_5$ represents the group $C|CR_8$ where $R_8$ is an unsubstituted phenyl group.

12. A compound as claimed in claim 7 in which $R_7$ represents a phenyl group optionally substituted by one or two chlorine or bromine atoms.

13. A compound as claimed in claim 7 in which $R_5$ represents the group $C|CR_8$ where $R_8$ is a phenyl group substituted by one halogen atom.

14. A compound as claimed in claim 7 in which $R_5$ represents the group $C|CR_8$ where $R_8$ is a phenyl group substituted by $C_{1-4}$ alkoxy groups.

15. A compound as claimed in claim 7 in which $R_7$ represents pyridyl.

16. A compound as claimed in claim 7 in which $R_5$ represents the group $C|CR_8$ where $R_8$ is a phenyl group substituted by a $C_{1-4}$ alkyl group.

17. A compound as claimed in claim 1 in which $R_2$ and $R_3$ each independently represent a $C_{1-6}$ straight or branched chain alkoxyalkyl group.

18. A composition for treating cardiovascular disorders resulting from transmembranal calcium ion flux comprising an effective amount of at least one compound as defined in claim 1 and a physiologically acceptable carrier.

* * * * *